United States Patent [19]

Allain et al.

[11] 4,309,556

[45] Jan. 5, 1982

[54] PREPARATION OF HEXAMETHYLDISILANE (HMDS) FROM CHLOROMETHYLDISILANES USING SPECIAL SOLVENTS

[75] Inventors: Ronald J. Allain, Naperville, Ill.; Joseph P. Maniscalco, Sugar Land, Tex.

[73] Assignee: Nalco Chemical Company, Oak Brook, Ill.

[21] Appl. No.: 171,768

[22] Filed: Jul. 24, 1980

[51] Int. Cl.$^3$ ................................................ C07F 7/08
[52] U.S. Cl. .................................................. 556/430
[58] Field of Search ........................................ 556/430

[56] References Cited

U.S. PATENT DOCUMENTS 2,908,698 10/1959 Kuriyagawa et al. ............. 556/430
2,923,633 2/1960 Stedman ........................ 556/430 X
3,277,047 10/1966 Selin ............................. 556/430 X
3,453,303 7/1969 Selin ............................. 556/430

OTHER PUBLICATIONS

Steudel et al., "J.A.C.S.," 82, pp. 6129-6132, 12/1960.

*Primary Examiner*—Paul F. Shaver
*Attorney, Agent, or Firm*—John G. Premo; Robert A. Miller

[57] ABSTRACT

An improved process for producing hexamethyldisilane by reacting ether solutions of methyl Grignard with a crude mixture of chloromethyl disilanes, the improvement which comprises obtaining higher yields and simplified purification of HMDS by the use of a mixed solvent system composed of tetrahydrofuran and the diethyl ether of tetraethylene glycol.

3 Claims, No Drawings

PREPARATION OF HEXAMETHYLDISILANE (HMDS) FROM CHLOROMETHYLDISILANES USING SPECIAL SOLVENTS

INTRODUCTION

The present invention is directed to an improved method for producing hexamethyldisilane. Hexamethyldisilane is produced by the reaction of methyl Grignard reagent with methylchlorodisilanes. This reaction is normally conducted in the presence of an ether such as diethyl ether, ethyl propyl ether, THF and the like. This synthetic method is described in the publication, *Organohalosilanes, Precursors to Silicones*, by R. J. H. Voorhoeve, 1967, pp. 9–16.

In conducting reactions of the type described in this reference, one of the problems that is encountered is that the byproduct, magnesium chloride, produced by the reaction precipitates from the ether reaction medium making recovery of the desired product of the reaction difficult and the optimum yields unattainable. If it were possible to improve the above reaction whereby product recovery could be simplified and improved and the yields increased, a valuable contribution would be made to the art.

PRIOR ART STATEMENT

The following prior art is believed to be pertinent to this invention. The Grignard reaction is well known in the literature. For example, reference may be made to a textbook entitled, *Organohalosilanes, Precursors to Silicones*, authored by R. J. H. Voorhoeve, 1967, pages 9–16. However, in this reference, no mention is made of solvents other than diethyl ether, THF, and some polyethers generally known as glymes. No mention is made of any combination of solvents, and particularly no mention is made of the use of the diethyl ethers of tetraethylene glycol (DETEG).

Also of interest are U.S. Pat. Nos. 3,312,605, 3,983,224, and 3,359,291 which teach the use of applicant's ether solvent combination in the synthesis of tetraalkyl lead compounds or in the generation of anhydrous magnesium chloride. Obviously, these alkyl lead compounds are not the silane compounds produced by the practice of the instant invention, nor does the instant invention necessarily recover anhydrous $MgCl_2$.

THE INVENTION

This invention is an improved process for producing hexamethyldisilane (HMDS) by reacting ether solutions of methyl Grignard reagent with a crude mixture of chloromethyldisilanes, the improvement which comprises obtaining higher yields and simplified purification of HMDS by the use of mixed solvent systems composed of tetrahydrofuran (hereinafter referred to as THF), and the diethyl ether of tetraethylene glycol (hereinafter referred to as DETEG).

This process is found to be most improved when the weight ratio of THF/DETEG is controlled between 25/75 to 75/25. A preferred weight ratio is 60 weight percent THF and 40 weight percent DETEG.

Ether Solvent System

The ether solvent system that has been found to be most beneficial is one containing a mixture of THF and DETEG because the diethyl ether of tetraethylene glycol (DETEG) maintains the byproduct, magnesium chloride, in solution, and by eliminating the difficulty normally encountered when this byproduct would precipitate during the reaction of methyl Grignard and chloromethyldisilane, product recovery and overall reaction efficiency are improved. The solvent system, THF/DETEG, has been found useful in previous applications involving the electrochemical synthesis of tetraalkyl lead compounds; U.S. Pat. Nos. 3,312,605 and 3,359,291 are incorporated herein by reference. These solvent systems have the unique ability to maintain high concentrations of anhydrous magnesium chloride in solution as is taught in U.S. Pat. No. 3,983,224 which is incorporated herein by reference. This assists not only in allowing electrolysis to produce tetraalkyl lead compounds as taught in the above references, but it is also found to be of critical importance in the instant invention.

By using a combination of THF and the diethyl ether of tetraethylene glycol as a solvent for methyl Grignard reagent and a mixture of the methylchlorodisilane compound, methylation reactions occurring to produce hexamethyldisilane are found to be improved not only in yield but also in ease of isolation and purification of the desired hexamethyldisilane compound.

The magnesium chloride byproduct generated in this reaction has been found to precipitate, solidify, and generally make the completion of the Grignard methylation reaction almost impossible.

It has also been found that the use of THF alone will allow the use of only very diluted Grignard reagents (less than 0.5 molar) in order to complete the methylation reaction without byproduct precipitation difficulties and lowered yields. By using a combination of THF with DETEG, we are able to obtain a reaction mixture from Grignard reagent in excess of 2.0 molar $CH_3MgCl$. Throughout the reaction of this Grignard reagent with the methylchlorodisilane mixture, no precipitation is observed and simple product isolation may be achieved by either distillation or a water wash, followed by organic/aqueous phase separation.

The use of this unique solvent combination also allows the recycle and recovery of both the THF and the DETEG and possible recovery of high grade anhydrous magnesium chloride.

The Methylchlorodisilane

While the literature reports the above described reaction using pure methylchlorodisilane, we have found that our invention allows the utilization of a crude methylchlorodisilane. Such a material, after appropriate treatment, has the following average composition: $(CH_3)_{2.5}Si_2Cl_{3.5}$.

This material can be obtained from commercial side streams and may be further treated prior to its use in the methylation reaction of the instant invention by one or two separate techniques.

Firstly, the crude material may be distilled with collection of the materials distilling between 135° C. to about 160° C. This middle distillate fraction is represented by the average stoichiometric formula above, i.e. $(CH_3)_{2.5}Si_2Cl_{3.5}$. The materials that distill prior to 135° C. are normally and generally monosilane compounds of chloro, methyl substitutions and simply would not yield the disilane compounds which are desirable in the instant invention. In fact, these monosilane compounds would require additional Grignard reagent and would subsequently give lower economical returns unless the distillation was accomplished.

The materials remaining after the 160° C. overhead boiling point has been reached normally would be polysilane compounds and, again, would not yield the disilane compounds of interest.

Secondly, a simple distillation which removes only those compounds boiling below 135° C. can be accomplished. The amount of polysilane compounds previously mentioned is relatively small and does not contribute drastically to the overall economics desired in the methylation reaction to produce hexamethyldisilane. Therefore, the preferred preparation of the crude chloromethyldisilane is to simply achieve a flash distillation removing low boiling components which, as previously taught, are primarily simply chloromethylmonosilane compounds prior to the reaction of the remaining chloromethyldisilane compounds with methyl Grignard reagent in the mixed ether solvent system of the invention.

EXAMPLES

The instant invention may be demonstrated by the following examples:

EXAMPLE 1

Distillation of crude chloromethyldisilane mixtures:

A twelve-foot-tall, two-inch ID glass column was constructed which contained eight feet of stainless steel protruded packing. Reflux rate was controlled by a Flexopulse timer and a magnetic distilling head. A 22 l. glass flask served as the distillation pot.

About 17 l. of the "mixture" was charged into the glass pot and heating was initiated using a Glas-Col heating mantle. Reflux rates varied from 0.2 to 3 with a maximum take-off of distillate of about 0.7 gallons/hour. All silanes collected below 135° C. boiling point were called "lights" (mainly methylchloromonosilanes). Silanes boiling from 135° C. to about 160° C. were collected and called distilled "mixtures" of the disilane fraction. Remaining silanes in the pot contained unidentified higher boiling silanes (probably polysilanes).

The column was kept under inert gas at all times since chlorosilanes, in general, are air and moisture sensitive.

EXAMPLE II

To a 22 l. glass flask was added 9.96 kg. of a 2.53 molar methyl Grignard in THF, and 3.46 kg. of DETEG. The mixture was stirred, cooled, and maintained under an inert gas. Slowly, 1.52 kg. of distilled "mixture" was added over a two-hour period. Temperatures ranged from 25° C. to 50° C. during addition.

After methylation, the reaction must be hydrolyzed. The mixture was pumped into a 20-gal. Pfaudler reactor and chilled. Slowly to it was added 5.6 kg. of aqueous 2% HCl. After hydrolysis, the organic layer was repeatedly washed with water to remove THF and DETEG. The hexamethyldisilane (HMDS) was then allowed to stand over 3-A molecular sieves to remove suspended water.

EXAMPLE III

Distillations, using the large packed column previously described, were run, and large quantities of distilled "mixture" and topped "mixture" were collected. Each type of "mixture" was then reacted and compared to undistilled "mixture" for the various reactions needed to obtain TMDS.

Methylation Reaction:

The methylation reaction can be written as follows for distilled "mixture":

$$Me_{2.5}Si_2Cl_{3.5} + 3.5\ MeMgCl \rightarrow Me_6Si_2 + 3.5\ MgCl_2$$

One mole of Grignard reacts with a mole of chloride. All calculations were based on Grignard consumed and chloride content of the disilane. When undistilled "mixture" is methylated, HMDS is obtained with other methylated silanes. Undistilled "mixture" contains methylchloromonosilanes and methylchloropolysilanes (such as $Si_3$, cyclic, etc.) in addition to the disilane fraction. Methylation of these is a waste of Grignard and also makes purification of HMDS more difficult.

After methylating the "mixture," the HMDS must be extracted from the solvents. This involved, first, a hydrolysis with 3% aqueous HCl, followed by repeated water washing. The hydrolysis step with the dilute HCl completely extracts all $MgCl_2$ with some DETEG and THF. This resulting brine is about 30% $MgCl_2$ with a density of 1.25 at 70° F. The top layer is then easily separated and washed until pure HMDS is obtained free of solvents. Workup of HMDS made from undistilled "mixture" is more difficult because of emulsion problems (due to impurities). HMDS made from topped "mixture" presented no problems during workup.

Purified HMDS was allowed to stand over either anhydrous $Na_2SO_4$ or 3-A molecular sieves. This removed suspended water from the HMDS. 3-A sieve was regenerated for repeated use.

EXAMPLE IV

The reactions mentioned above for the methylation of the distilled mixtures could be achieved without the addition of DETEG. However, precipitation and solidification of magnesium chloride and its etherate complexes would prevent stirring and thus hinder the reaction. THF/DETEG rations of 60/40 to 80/20 were examined. With an 80/20 ratio some magnesium chloride does precipitate, but the reaction may still be stirred and the yields are not adversely affected. With a solvent ratio of THF to DETEG (on a weight to weight basis) of less than 75/25, all magnesium chloride by-product is solubilized. However, with the 75/25 ratio, completed methylation results in two liquid layers. The top layer contains mostly hexamethyldisilanes with some THF. The bottom layer contains THF, DETEG, and a small amount of HMDS, along with by-product, magnesium chloride.

When the optimum solvent ratio is used, that ratio being 60 weight percent THF/40 weight percent DETEG, a clear one-phase solution results.

In addition, the use of the mixed ethers maximizes the concentration of active Grignard which can be used to accomplish the methylation of the chloromethyldisilane mixtures.

For all three types of mixtures, that is, undistilled, distilled "heart cut," and flash topped, Grignard stoicheometry was based on chloride content of the disilane mixture. In all methylations, an excess amount of Grignard was used. Yields are calculated on moles of Grignard consumed and chloride moles charged. Table I compares the methylation data for the three types of mixtures.

TABLE I

METHYLATION DATA FROM UNDISTILLED, DISTILLED, AND TOPPED MIXTURES

| Silane Starting Material | $\frac{A}{B}$ | $\frac{C}{B}$ | $\frac{D}{B}$ | $\frac{E}{B}$ | F | G |
|---|---|---|---|---|---|---|
| Undistilled | 3.78 | 3.82 | 4.07 | 0.45 | 80.7 | — |
| Distilled | 3.80 | 3.54 | 4.01 | 0.54 | 93.0 | 95.6 |
| Topped | 3.90 | 3.78 | 4.18 | 0.52 | 91.6 | |

A = Cl⁻ moles reacted (of the silane)
B = HMDS moles produced
C = OH moles reacted (of the Grignard)
D = Total Grignard moles charged
E = Excess moles of Grignard
F = HMDS % purity after water washing
G = HMDS % yields

We claim:

1. An improved process for producing hexamethyldisilane (HMDS) by reacting ether solutions of methyl Grignard reagent with a crude mixture of chloromethyldisilanes, the improvement which comprises obtaining higher yields and simplified purification of HMDS by the use of mixed ether solvent systems composed of tetrahydrofuran and the diethyl ether of tetraethylene glycol.

2. The process of claim 1 wherein the tetrahydrofuran and diethyl ether of tetraethylene gylcol are present in a weight ratio from 25/75 to 75/25.

3. The process of claim 1 wherein the weight ratio of THF to DETEG is 60 weight percent THF and 40 weight percent DETEG.

* * * * *